United States Patent
Lee et al.

(10) Patent No.: US 12,364,422 B2
(45) Date of Patent: Jul. 22, 2025

(54) BODY-INSERTION DEVICE

(71) Applicant: AIRS MEDICAL CO., LTD., Seoul (KR)

(72) Inventors: Hye Seong Lee, Seoul (KR); Yun Myeong Kim, Seoul (KR)

(73) Assignee: AIRS MEDICAL CO., LTD., Seoul (KR)

(*) Notice: Subject to any disclaimer, the term of this patent is extended or adjusted under 35 U.S.C. 154(b) by 268 days.

(21) Appl. No.: 17/850,887

(22) Filed: Jun. 27, 2022

(65) Prior Publication Data
US 2022/0322982 A1 Oct. 13, 2022

Related U.S. Application Data (63) Continuation of application No. PCT/KR2020/009393, filed on Jul. 16, 2020.

(30) Foreign Application Priority Data

Apr. 2, 2020 (KR) .................. 10-2020-0040097

(51) Int. Cl.
*A61B 5/153* (2006.01)
*A61B 5/00* (2006.01)
*A61B 5/15* (2006.01)

(52) U.S. Cl.
CPC ...... *A61B 5/1535* (2013.01); *A61B 5/150748* (2013.01); *A61B 5/489* (2013.01)

(58) Field of Classification Search
CPC ......... A61B 8/4218; A61B 8/54; A61B 5/489; A61B 5/150748; A61B 17/3403
See application file for complete search history.

(56) References Cited

U.S. PATENT DOCUMENTS

| | | | |
|---|---|---|---|
| 4,619,249 | A | 10/1986 | Landry |
| RE33,234 | E | 6/1990 | Landry |
| 9,364,171 | B2 | 6/2016 | Harris et al. |
| 9,913,605 | B2 | 3/2018 | Harris et al. |

(Continued)

FOREIGN PATENT DOCUMENTS

| | | |
|---|---|---|
| CN | 101171046 A | 4/2008 |
| EP | 2 170 204 A2 | 4/2010 |

(Continued)

OTHER PUBLICATIONS

KR-20100121277-A English Translation (Year: 2010).*

*Primary Examiner* — Ashley K Buran
*Assistant Examiner* — Helene Bor
(74) *Attorney, Agent, or Firm* — McDonald Hopkins LLC (57) ABSTRACT

The present disclosure provides a body-insertion device for a body, which comprises a first moving unit for moving an image acquisition unit; an insertion unit; and a second moving unit for moving the insertion unit. The first moving unit comprises at least one of a 1-1 module for moving the image acquisition unit in a 1-1 direction, a 1-2 module for moving the image acquisition unit in a 1-2 direction, and a 1-3 module for moving the image acquisition unit in a 1-3 direction. The second moving unit comprises at least one of a 2-1 module for moving the insertion unit in a 2-1 direction, a 2-2 module for moving the insertion unit in a 2-2 direction, and a 2-3 module for moving the insertion unit in a 2-3 direction.

7 Claims, 5 Drawing Sheets

(56) References Cited

U.S. PATENT DOCUMENTS

| | | |
|---|---|---|
| 10,238,327 B2 | 3/2019 | Harris et al. |
| 2003/0187345 A1 | 10/2003 | Mochizuki |
| 2004/0133168 A1* | 7/2004 | Salcudean .......... A61B 17/3478 604/164.13 |
| 2008/0167674 A1* | 7/2008 | Bodduluri ......... A61M 37/0069 606/187 |
| 2008/0275396 A1 | 11/2008 | Neerken et al. |
| 2010/0036245 A1* | 2/2010 | Yu ........................ A61N 5/1027 600/7 |
| 2010/0234856 A1* | 9/2010 | Stoianovici ............ A61B 34/70 606/130 |
| 2010/0274202 A1 | 10/2010 | Hyde et al. |
| 2011/0301500 A1 | 12/2011 | Maguire et al. |
| 2012/0190981 A1* | 7/2012 | Harris ...................... A61B 5/14 604/95.01 |
| 2013/0035591 A1 | 2/2013 | Hyde et al. |
| 2013/0041253 A1 | 2/2013 | Hyde et al. |
| 2014/0107569 A1* | 4/2014 | Fischer .................. A61B 34/37 604/95.01 |
| 2014/0180066 A1 | 6/2014 | Stigall |
| 2014/0275990 A1 | 9/2014 | Hagy et al. |
| 2014/0343406 A1 | 11/2014 | Damjanjovic |
| 2015/0297177 A1* | 10/2015 | Boctor .................. A61B 34/30 901/47 |
| 2015/0313675 A1* | 11/2015 | Lipov .................. A61B 8/0841 600/424 |
| 2015/0374273 A1 | 12/2015 | Maguire et al. |
| 2016/0157887 A1 | 6/2016 | Kim et al. |
| 2016/0256093 A1 | 9/2016 | Harris et al. |
| 2017/0007200 A1 | 1/2017 | Hagy et al. |
| 2017/0188990 A1 | 7/2017 | Von Allmen et al. |
| 2017/0252002 A1 | 9/2017 | Mine et al. |
| 2018/0146904 A1 | 5/2018 | Harris et al. |
| 2019/0357828 A1 | 11/2019 | Harris et al. |
| 2020/0015899 A1 | 1/2020 | Scheib et al. |

FOREIGN PATENT DOCUMENTS

| | | | |
|---|---|---|---|
| EP | 2654593 | B4 | 11/2020 |
| JP | 08-173433 | A | 7/1996 |
| JP | 08-229046 | A | 9/1996 |
| JP | 2004-000499 | A | 1/2004 |
| JP | 2008-539932 | A | 11/2008 |
| JP | 2016-501635 | A | 1/2016 |
| JP | 2016-512137 | A | 4/2016 |
| JP | 2018-202042 | A | 12/2018 |
| JP | 2019-084088 | A | 6/2019 |
| KR | 10-2010-0120403 | A | 11/2010 |
| KR | 20100121277 | A * | 11/2010 |
| KR | 10-1362922 | B1 | 2/2014 |
| KR | 10-1389993 | B1 | 5/2014 |
| KR | 10-1500273 | B1 | 3/2015 |
| KR | 2015-0133449 | A | 11/2015 |
| KR | 10-1601421 | B1 | 3/2016 |
| KR | 10-2016-0046012 | A | 4/2016 |
| KR | 10-2016-0069180 | A | 6/2016 |
| KR | 10-1862133 | B1 | 6/2018 |
| KR | 10-2019-0131989 | A | 11/2019 |
| KR | 10-2143179 | B1 | 8/2020 |
| KR | 1022469660000 | A | 4/2021 |
| KR | 10-2362087 | B1 | 2/2022 |
| WO | 00/56213 | A1 | 9/2000 |
| WO | 2006/120619 | A2 | 11/2006 |
| WO | 2008/081438 | A1 | 7/2008 |
| WO | 2008/085756 | A2 | 7/2008 |
| WO | 2009/004616 | A2 | 1/2009 |
| WO | 2009/004616 | A3 | 1/2009 |
| WO | 2009/004616 | A9 | 1/2009 |
| WO | 2010/056538 | A1 | 5/2010 |
| WO | 2012/088471 | A1 | 6/2012 |
| WO | 2014/143650 | A1 | 9/2014 |
| WO | 2015/179505 | A1 | 11/2015 |
| WO | 2016/060308 | A1 | 4/2016 |

* cited by examiner

BODY-INSERTION DEVICE

CROSS-REFERENCE TO RELATED APPLICATION

This application is a Continuation of International Application No. PCT/KR2020/009393, filed on Jul. 16, 2020, which claims priority to Korean Application No. 10-2020-0040097, filed on Apr. 2, 2020. The aforementioned applications are incorporated herein by reference in their entireties.

TECHNICAL FIELD

The present disclosure relates to a body-insertion device. Specifically, the present disclosure relates to a device which moves an insertion unit to the location which is determined as a point of insertion through image analysis based on the image obtained by an image acquisition unit and then insert a medical instrument such as a venipuncture needle into the body at the location.

RELATED ART

In hospitals or clinics, a medical procedure that a medical instrument is inserted into a body are frequently performed for various purposes. For example, a venipuncture needle is inserted into a superficial vein for blood collection or intravenous injection and a catheter is inserted into some organs. In this specification, a venipuncture needle or blood collection needle is simply referred to as "needle" for brevity. Currently, a medical doctor, a nurse or a pathologist who is trained to find the location of blood vessel such as a superficial vein performs the insertion. The current system needs a long time for training the medical staffs and labor costs are incurred. Further, if a needle is not inserted at an appropriate location, the medical staff additionally tries to insert the needle into the body and a person whom the needle is inserted may experience unnecessary pain due to the additional needle insertion. Even a specialist has difficulties when inserting a needle into a person with poor blood vessel conditions such as a baby, an old person, a patient undergoing chemotherapy, a person having dark skin, and the like.

Repeated blood collection work can cause high fatigue and a lot of discomfort even for the experienced medical staffs. Further, a medical staff performing blood collection is exposed to infection risks when blood splashes onto the staff or enters the staff's body during the blood collection procedure.

The applicant filed a Korean Patent Application No. 10-2020-0010302 on Jan. 29, 2020 (KR Patent No. 10-2246966) for a method for exactly detecting a location of a target of a body such as a superficial vein by use of a machine learning. The application is incorporated herein in its entirety as an example of a method for detecting a location to be inserted by use of image analysis and machine learning.

PRIOR ART REFERENCES

Korean Patent No. 10-1601421 (Title: Automatic Method of Blood Collecting; Published on Mar. 10, 2016)
Korean Patent No. 10-1362922 (Title: Module for Launching Blood Lancet and Apparatus having the Same)

SUMMARY

The object of the present disclosure is to provide a body-insertion device which detects an organ to be inserted and inserts a medical instrument into the organ.

In order to accomplish the object, the present disclosure provides a body-insertion device for a body, which comprises a first moving unit for moving an image acquisition unit; an insertion unit; and a second moving unit for moving the insertion unit. The first moving unit comprises at least one of a 1-1 module for moving the image acquisition unit in a 1-1 direction, a 1-2 module for moving the image acquisition unit in a 1-2 direction, and a 1-3 module for moving the image acquisition unit in a 1-3 direction. The second moving unit comprises at least one of a 2-1 module for moving the insertion unit in a 2-1 direction, a 2-2 module for moving the insertion unit in a 2-2 direction, and a 2-3 module for moving the insertion unit in a 2-3 direction.

At least one of the 1-2 module to the 1-3 module can comprise a driving unit and an object to be driven by the driving unit. The object can be connected to the image acquisition unit or the insertion unit to move the unit in accordance with the control of the driving unit. The object can be at least one of a timing belt extending between at least two pulleys driven by the driving unit, a screw driven by the driving unit, and rack/pinion driven by the driving unit.

The 1-1 direction can be a transvers direction of a body portion to be inserted; the 1-2 direction can be a height direction of the body portion; and the 1-3 direction can be a rotation direction which is a longitudinal direction of the body portion.

The 2-1 direction can be a transverse direction of a body portion to be inserted; the 2-2 direction can be a height direction of the body portion; and the 2-3 direction can be a direction having a predetermined angle with respect to a longitudinal direction of the body portion.

The device of the present disclosure can further comprise a 2-4 module for adjusting the predetermined angle, which rotates the insertion unit about at least one of the 2-1 direction and the 2-2 direction.

The image acquisition unit can be selected from a group consisting of an ultrasound probe, a photoacoustic imaging device, ToF sensor (time of flight sensor) comprising a near-infrared light emitting diode for recognizing the position coordinate of light reflected from the inside of a body, CT and MRI.

The second moving unit can comprise a sensor for detecting inlet of blood.

The device of the present disclosure can further comprise at least one of a 1-4 module for rotating the image acquisition unit about the 1-2 direction, and a 1-5 module for moving the image acquisition unit along the longitudinal direction of a body portion to be inserted.

The device of the present disclosure can further comprise a position sensor for detecting the position of component which is moved by the first moving unit or the second moving unit and a distance sensor for measuring the relative distance between the components.

At least one of the components which is moved by the first moving unit or the second moving unit can comprise an electronic tag for recognition of position.

The present disclosure can also provide a computer-implemented method for controlling the body-insertion device, which comprises a first step of moving the image acquisition unit to a body portion to be inserted by driving at least one of the 1-1 module to the 1-3 module; a second step of determining the location of the organ to be inserted based on the analysis of the image acquired by the image acquisition unit; and a third step of inserting a medical instrument of the insertion unit at the determined location by driving at least one of the 2-1 module to the 2-3 module.

The method can further comprise a fourth step of recognizing an extending path of the organ by rotating the image acquisition unit about the 1-2 direction or moving the mage acquisition unit along the longitudinal direction of the body portion.

The method can further comprise a fifth step of measuring the pressure applied to the body portion by the image acquisition unit.

The present disclosure can also provide a computer-implemented system comprising one or more processors and one or more computer-readable media storing computer-executable instructions that, when executed, cause the one or more processors to perform the method of the present disclosure.

The present disclosure can also provide a computer program product comprising one or more computer-readable storage media and program instructions stored in at least one of the one or more storage media, the program instructions executable by a processor to cause the processor to perform the method of the present disclosure.

The present disclosure provides the computer program product performing the method of the present disclosure.

It should be understood that the above-referenced drawings are not necessarily to scale, presenting a somewhat simplified representation of various preferred features illustrative of the basic principles of the disclosure. The specific design features of the present disclosure will be determined in part by the particular intended application and use environment.

DETAILED DESCRIPTION

Hereinafter, the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

In this specification, the order of each step should be understood in a non-limited manner unless a preceding step must be performed logically and temporally before a following step. That is, except for the exceptional cases as described above, although a process described as a following step is preceded by a process described as a preceding step, it does not affect the nature of the present disclosure, and the scope of rights should be defined regardless of the order of the steps. In addition, in this specification, "A or B" is defined not only as selectively referring to either A or B, but also as including both A and B. In addition, in this specification, the term "comprise" has a meaning of further including other components in addition to the components listed.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled," "connected," or "fastened" denotes a physical relationship between two components whereby the components are either directly connected to one another or indirectly connected via one or more intermediary components.

The terms "first," "second," or the like are herein used to distinguishably refer to same or similar elements, or the steps of the present disclosure and they may not infer an order or a plurality.

In this specification, the essential elements for the present disclosure will be described and the non-essential elements may not be described. However, the scope of the present disclosure should not be limited to the invention including only the described components. Further, it should be understood that the invention which includes additional element or does not have non-essential elements can be within the scope of the present disclosure.

The method of the present disclosure can be an electronic arithmetic device.

The electronic arithmetic device can be a device such as a computer, tablet, mobile phone, portable computing device, stationary computing device, server computer etc. Additionally, it is understood that one or more various methods, or aspects thereof, may be executed by at least one processor. The processor may be implemented on a computer, tablet, mobile device, portable computing device, etc. A memory configured to store program instructions may also be implemented in the device(s), in which case the processor is specifically programmed to execute the stored program instructions to perform one or more processes, which are described further below. Moreover, it is understood that the below information, methods, etc. may be executed by a computer, tablet, mobile device, portable computing device, etc. including the processor, in conjunction with one or more additional components, as described in detail below. Furthermore, control logic may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The components of the device can any shape, size, or dimension as well as those which are clearly illustrated in the appended drawings if they can perform the intended functions of the present disclosure. Further, the number of the components of the present disclosure can be differently selected as needed in the extent that it makes the device operable.

In this specification, the embodiments that the body-insertion device is used for a blood vessel are mainly described. However, it should be understood that the organ to be inserted by a medical instrument can be nerves, arteries, and the like and is not limited to the blood vessel.

Figure 1:
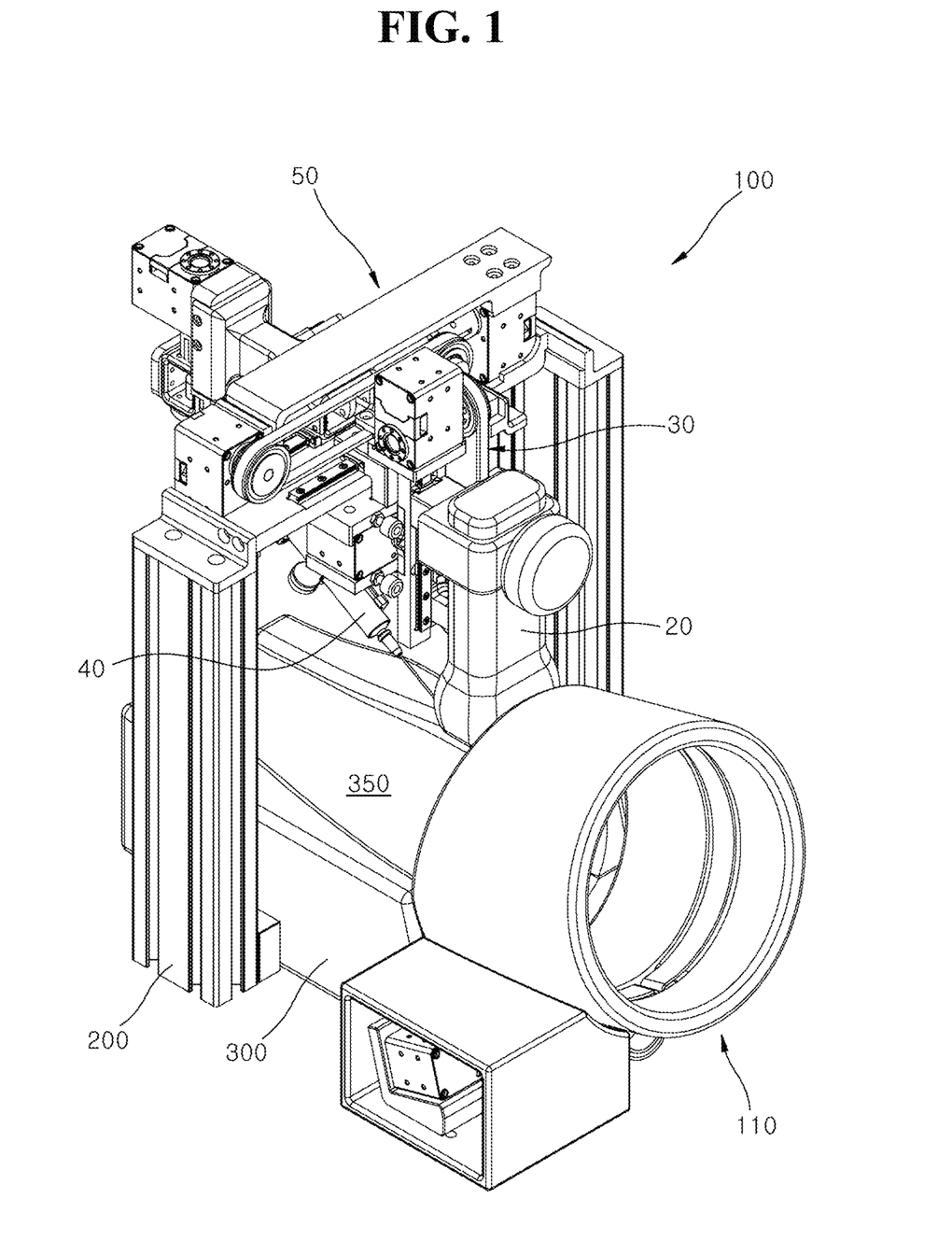
FIG. 1 is a perspective view of the body-insertion device according to the present disclosure.
Figure 2:
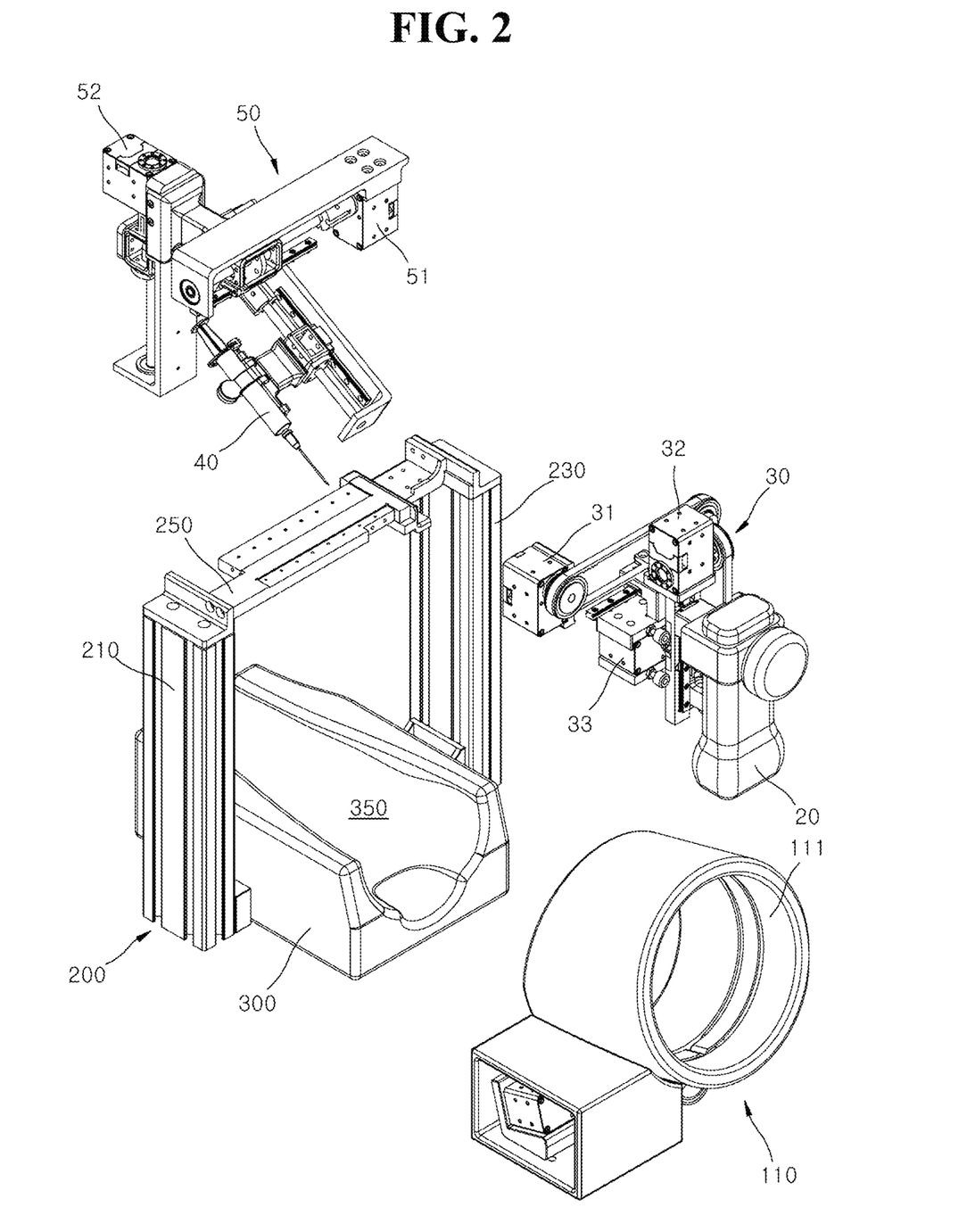
FIG. 2 is an exploded perspective view of the body-insertion device according to the present disclosure.

FIG. 1 is a perspective view of a body-insertion device (100) of the present disclosure; and FIG. 2 is an exploded perspective view of the device, where main units thereof are disassembled. The body-insertion device (100) comprises an image acquisition unit (20), a first driving unit (30) for moving the image acquisition unit (20), an insertion unit (40), a second driving unit (50) for moving the insertion unit (40), a body holding unit (110), a frame (200) and a body placing unit (300).

The image acquisition unit (20) is a unit for recognizing the inside of a body, for example, an ultrasound probe, a photoacoustic imaging device, a ToF (Time of Flight Sensor) which has a near-infrared light emitting diode for recognizing the position coordinate of light reflected from the inside of a body, CTs, MRIs, and the like. However, the image acquisition unit is not limited to the listed examples.

The body holding unit (110) holds the body portion while a needle is inserted. The body holding unit can hold an upper arm in the event that the device is used for collecting blood.

The frame (200) can comprise a pair of spaced posts (210, 230), a horizontal bar (250) which extends between the posts (210, 230). The horizontal bar (250) is provided with a first guide fixing portion (253) and a second guide fixing portion (251).

The body placing unit (300) is a unit where a body portion to be inserted by a needle is placed. A lower arm is placed thereto in the event that the device is used for collecting blood.

Figure 3:
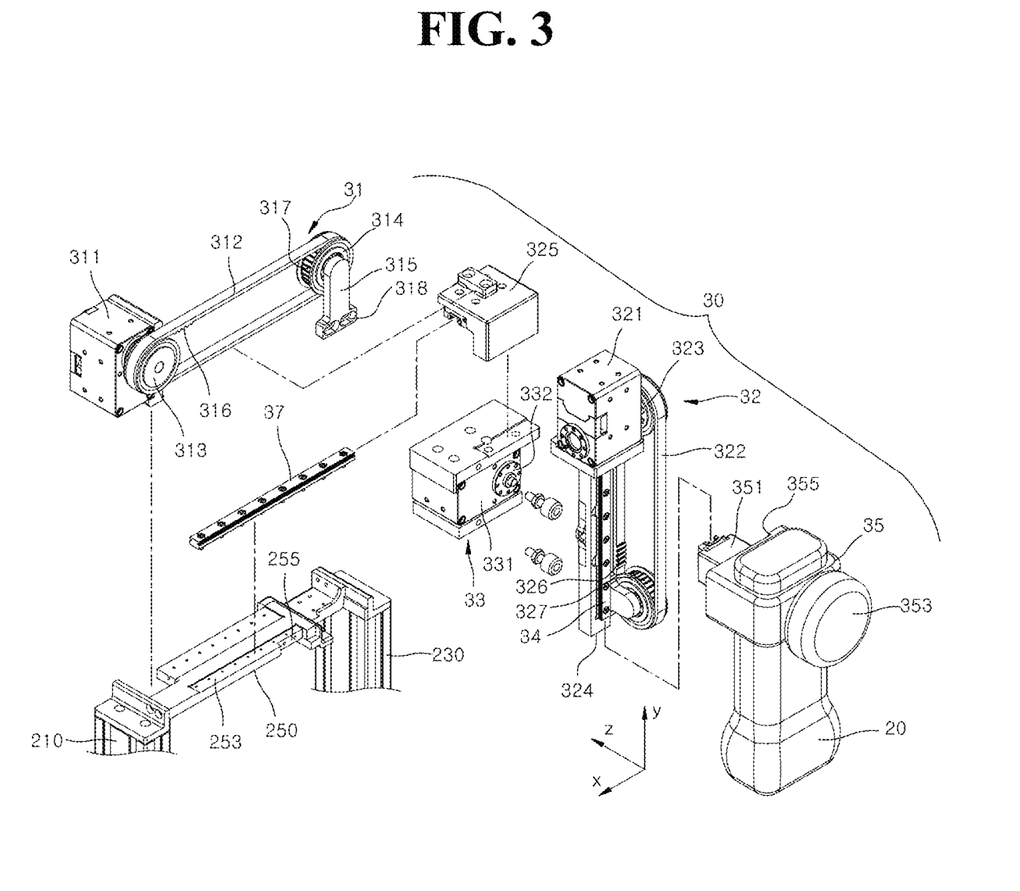
FIG. 3 is an exploded perspective view of a first moving unit of the present disclosure.

FIG. 3 is an exploded perspective view of the first moving unit (30). The first moving unit (30) comprises a 1-1 module (31) for moving the image acquisition unit (20) in a 1-1 direction, a 1-2 module (32) for moving the image acquisition unit (20) in a 1-2 direction, and a 1-3 module (33) for moving the image acquisition unit (20) in a 1-3 direction. Although it is illustrated and described that the modules are individually provided, they can be incorporated into one module. Alternatively, the modules can be constituted into two modules which includes a first module moving the image acquisition unit along two directions and a second module moving the image acquisition unit along the remaining one direction.

The 1-1 direction (x-axis direction) is the transverse direction of the body portion to be inserted by a needle; the 1-2 direction (y-axis direction) is the height direction of the body portion to be inserted by a needle; and the 1-3 direction is a rotation direction which is the longitudinal direction (z-axis direction) of the body portion to be inserted by a needle, i.e., the rotation direction on xy plane. The device (100) of the present disclosure can be used for collecting blood from blood vessels; can be used for intravenous injections; or can be used for inserting other medical parts such as a catheter into an organ. The device can be used for various medical purposes as well as the described ones.

The 1-1 module (31) comprises a driving unit (311), a pair of spaced pulleys (313, 314), a timing belt (312) which extends between the pulleys, a fixing portion (315), a first connecting portion of timing belt (325), and a guide (37). The timing belt (312) is provided with a teeth portion (316). The pulleys (313, 314) are provided with a teeth portion (317) which can mesh with a teeth portion (316). The timing belt (322) and the pulleys (323, 327) of the 1-2 module (32) can be also provided with a teeth portion.

The term "driving unit" in this specification means a device for driving a driven object in a predetermined direction. It can be, for example, a motor, but is not limited to a specific device.

At least one of the pair of pulleys (313, 314) can be driven by the driving unit (311). The fixing portion (315) can be provided in at least one of the pair of pulleys (313, 314). For example, a mounting hole (318) provided under the fixing portion (315) and a mounting hole (255) provided on the horizontal bar (250) of the frame (200) are aligned with respect to each other and they are fastened by a bolt. The first connecting portion of timing belt (325) is connected to the timing belt (312) and is slidably provided on the guide (37). Further, the first connecting portion of timing belt (325) can be connected to the 1-3 module (33) as described in the below. The guide (37) extends along the 1-1 direction and can be fixed to a first guide fixing portion (253) of the horizontal bar (250).

In this specification, the term "a predetermined direction" should be construed to also include a direction having an angle with respect to the predetermined direction as well as the predetermined direction.

The driving unit (311) rotates the pulleys (313, 314), thereby causing the timing belt (312) to travel along the 1-1 direction (x direction), i.e., the transverse direction of the body portion to be inserted by a needle. The 1-3 module (33) which is connected to the timing belt (312) at the first connecting portion of timing belt (325) can move in the 1-1 direction along the guide (37). As described in the below, the image acquisition unit (20) can move in the 1-1 direction (x direction) by the 1-1 module (31) since the 1-3 module (33) is connected to the body (324) of the 1-2 module (32).

The 1-2 module (32) comprises a driving unit (321), a pair of spaced pulleys (323, 327), a timing belt which extends between the pair of pulleys (323, 327), a body (324), and a guide (34) provided in the body (324). At least one of the pair of pulleys (323, 327) can be driven by the driving unit (321). The guide (34) can extend on the body (324) along the 1-2 direction (y direction). The body (324) can be connected to the rotation axis (332) of the driving unit (331) of the 1-3 module (33) so as to rotate about z axis, i.e., rotate on the xy plane.

The device of the present disclosure can further comprise a holder (35) for holding the image acquisition unit (20). The holder (35) comprises a guide connecting portion (351) which is connected to the guide (34), a second connecting portion of timing belt (355) which is connected to the timing belt (322), and a fastening member (353) which fastens the image acquisition unit (20). The guide connecting portion (351) is provided to be slidable along with the guide (34).

The driving unit (321) rotates the pulleys (323, 327) so that the timing belt (322) travels along the 1-2 direction (y direction), i.e., the height direction of the body portion to be inserted by a needle. Then, the holder (35) which is connected to the timing belt (322) at the second connecting portion of timing belt (355) moves in the 1-2 direction along the guide (34). Consequently, the image acquisition unit (20) held by the holder (35) moves in the 1-2 direction.

The 1-3 module (33) comprises a driving unit (331) and an output shaft (332) thereof. The output shaft (332) is connected to the body (324) of the 1-2 module (32). When the driving unit (331) is turned on, the output shaft (332) rotates and then the body (324) can rotate about z axis, i.e., on the xy plane. When the body (324) rotates, the holder (35) connected to the body (324) and the image acquisition unit (20) can also rotate in the same direction.

In this specification, the expression 'rotate in a direction (or rotate about an axis)' and 'rotate on a plane' should be construed to also include 'rotate in a direction (or rotate about an axis) having an angle to the direction (or axis)' and 'rotate on a plane having an angle to the plane,' respectively.

The first moving unit (30) can further comprise an additional module (not illustrated) which moves the image acquisition unit (20) along z direction, i.e., the longitudinal direction of the body portion to be inserted by a needle and a rotating module (not illustrated) which rotates the image acquisition unit (20) on xz plane, i.e., about the 1-2 axis. The additional module can increase DOF (degree of freedom) of movement of the image acquisition unit (20) and help recognize the extending direction of blood vessel. The rotation module can also help recognize the extending direction of blood vessel as described in the below. The additional module can be incorporated into at least one of the 1-1 module (31) to the 1-3 module (33) or can be provided in a separate module.

Figure 4:
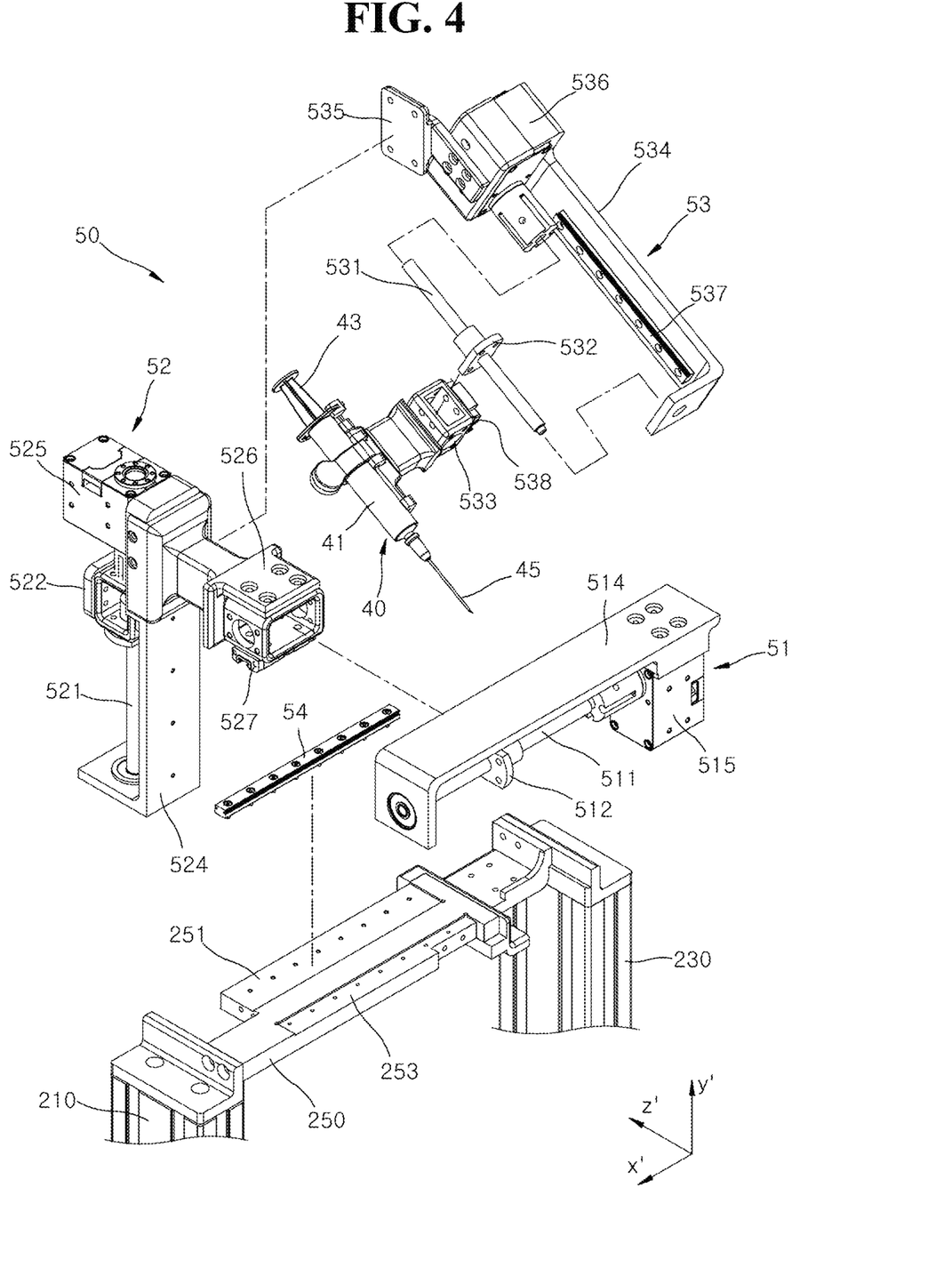
FIG. 4 is an exploded perspective view of a first moving unit of the present disclosure.

FIG. 4 shows an exploded perspective view of the second moving unit (50) of the device of the present disclosure.

The second moving unit (50) comprises a 2-1 module (51) which moves the insertion unit (40) in the 2-1 direction (x'), a 2-2 module (52) which moves the insertion unit (40) in the 2-2 direction (y'), and a 2-3 module (53) which moves the insertion unit (40) in the 2-3 direction (z'). The 2-3 direction can be the direction which has a predetermined angle to z' axis on the plane parallel toy 'z' plane.

Although the modules (51, 52, 53) are individually drawn and described, they can be incorporated into one module. Alternatively, the modules can be constituted into two modules which includes a first module moving the insertion unit (40) in two directions and a second module moving the insertion unit in the remaining one direction.

The 2-1 direction (x'), the 2-2 direction (y'), z' direction can be defined the same as the 1-1 direction (x), the 1-2 direction (y) and the 1-3 direction (z), respectively. In the preferred embodiments, the 2-3 direction can have an angle with respect to the 1-3 direction. The angle can be 5° to 60°, preferably 20° to 45°.

The 2-1 module (51) comprises a screw (511), a movable member (512) which moves along the screw when the screw rotates, a body (514), a driving unit (515) and a guide (54). The screw (511) extends along the 2-1 direction (x' direction). The movable member (512) is fixed at the fixing portion (526). The fixing portion (526) comprises a guide mounting portion (527) thereunder, which is slidably connected to the guide (54). The fixing portion (526) can be provided at the body (524) of the 2-2 module (52). The guide (54) extends along the 2-1 direction and can be fixed at the second guide fixing portion (251) of the horizontal bar (250) of the frame (200).

The driving unit (515) rotates the screw (511), thereby moving the movable member (512) in the 2-1 direction on the screw (511). Then, the fixing portion (526) is guided along the guide (54) and moves in the 2-1 direction. Further, the body (524) can move in the 2-1 direction. As described in the below, the 2-3 module (53) where the insertion unit (40) is provided is fixed at the 2-2 module (52). Consequently, the driving unit (515) can move the insertion unit (40) in the 2-1 direction.

The 2-2 module (52) comprises a screw (521), a movable member (522) which moves on the screw when the screw rotates, a body (524), a driving unit (525) and a fixing portion (526). The movable member (522) is fixed at the fixing portion (535) of the 2-3 module (53), thereby connecting the 2-2 module (52) with the 2-3 module (53). The screw (521) extends along the 2-2 direction (y' direction). The body (524) can be provided with a guide (not illustrated) where the movable member (522) is slidably connected.

The driving unit (525) rotates the screw (521) so that the movable member (522) is guided on the screw (521) and moves in the 2-2 direction. Thus, the 2-3 module (53) connected to the movable member (522) also moves in the 2-2 direction; and then the insertion unit (40) provided at the 2-3 module (53) can also move in the 2-2 direction.

The 2-3 module (53) comprises a screw (531), a movable member (532), a body (534), a fixing portion (535), a driving unit (536), and a guide (537) which extends along the 2-3 direction and is provided at the body (534). The screw (531) extends along the 2-3 direction. The movable member (532) is fixed at the fixing portion (533) provided at the insertion unit (40). The insertion unit (40) comprises a body (41), a piston (43), a needle (45) which is inserted into the body, and a fixing portion (533). The fixing portion (533) is provided with a guide mounting portion (538) which is slidably connected to the guide (537). The insertion unit (40) can further comprise a sensor (not illustrated) which detects inlet of blood. The sensor can detect the inlet of blood by sensing blood color or blood absorbance. The sensor can be provided in the second moving unit (50), not in the insertion unit (40).

The driving unit (536) rotates the screw (531), thereby moving the movable member (532) in the 2-3 direction on the screw (531). Then, the insertion unit (40) connected to the movable member (532) moves in the 2-3 direction along the guide (537).

The second moving unit (52) can further comprise an adjustment module (not illustrated) for adjusting the angle of the insertion unit (40). The angle of the insertion unit (40) can be adjusted by rotating the insertion unit (40) about y' axis or by rotating the insertion unit (40) about x' axis, i.e., on y'z' plane. The adjustment by the former rotation can increase the accuracy of blood collecting since the insertion unit (40) can be aligned with the extending direction of blood vessel when the needle is inserted into the body. The adjustment by the latter rotation can adjust the penetration depth of needle. The rotation about y' axis and the rotation about x' axis can be performed by one module or two or more modules which are individually provided. Alternatively, at least one of the 2-1 module to the 2-3 module can be configured to perform the rotation.

The timing belt is used in the 1-1 module (31) and the 1-2 module (32) for easy measurement of pressure applied to the component to be driven. The screw is used in the 2-1 module (51) to 2-3 module (53) for positioning precision of the component to be driven. However, those embodiments are just exemplary, and the scope of the present disclosure is not limited to those embodiments. The screw can be used in at least one of the 1-1 module (31) to the 1-3 module (33) as the component to be driven. Further, the timing belt can be used in at least one of the 2-1 module (51) to the 2-3 module (53) as the component to be driven. Alternatively, rack and pinion (not illustrated) can be also used as the components to be driven and other various mechanical parts can be used as the component to be driven.

Further, an electronic tag (not illustrated) can be provided in at least one of the holder (35), the insertion unit (40), the guide connecting portion (351), the first connecting portion of timing belt (325) or the like. In those embodiments, the position of components can be easily calculated from the position of the electronic tag, which is detected by a sensor or a camera.

A controller (not illustrated) can calculate the position of the components of the device of the present disclosure and control the operation of the components. The controller can be an electronic arithmetic device connected to the device of the present disclosure, for example, PCs, smartphones, tablets, and the like or a remotely connected server.

Figure 5:
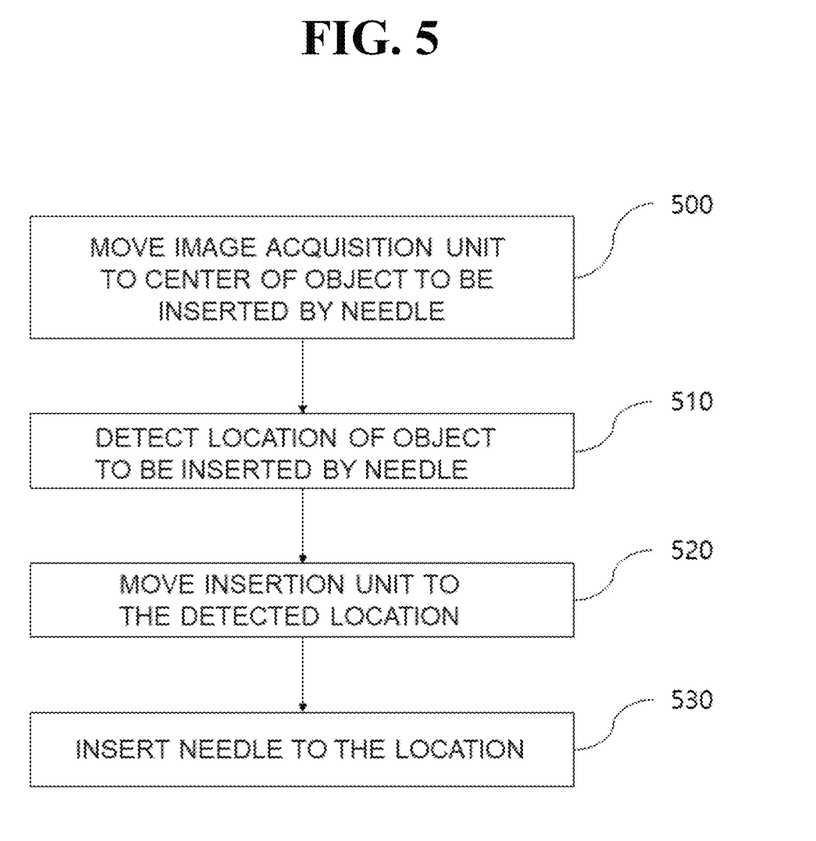
FIG. 5 is a flowchart of the body-insertion processes according to the present disclosure.

The operation of the device of the present disclosure will be described. Although the embodiments wherein the purpose of insertion into the body is blood collecting and the image acquisition unit (20) is an ultrasound probe are described for convenience of explanation, it should be understood that the scope of the present disclosure is not limited to those embodiments. The operations described in the below can be carried out by the controller (not illustrated) in accordance with the program codes conceived for the present disclosure. The insertion position can be determined based on the conventional image analysis method and machine learning, in particular, Convolutional Neural Network technologies.

For blood collection, the location of a superficial vein is determined; the insertion unit (40) is moved to the determined location; a needle is inserted to the vein at the location; and then blood is drawn through the needle.

A person passes an arm through the holding unit (110) and then places the arm in the placing portion (350). Subsequently, in the step (500), at least one of the 1-1 module (31) and the 1-2 module (32) is driven to move the image acquisition unit (20) to the body portion to be inserted by a needle. It is preferred that at the first time the image acquisition unit (20) is moved to the center of the body portion.

In the step (510), the location of the organ to be inserted by a needle, for example, a superficial vein, is determined. The location can be determined by, for example, the methods disclosed in Korean Patent Application No. 10-2020-0010302 (Patent No. 10-2246966) or other methods using the machine learning based on image analysis.

The image acquisition unit (20) is moved to the body portion to be inserted by a needle and comes into contact with the body portion. In an exemplary embodiment, the image acquisition unit (20) is moved in at least one of the 1-1 direction and the 1-3 direction to the location above the body portion. Subsequently, the driving unit (321) descend the image acquisition unit (20) in the 1-2 direction (y direction) so that the image acquisition unit comes into contact with the body portion. Whether the image acquisition unit (20) is in contact with the body portion can be recognized by sensing the load applied to the driving unit (321). In the event that the image acquisition unit (20) is an ultrasound probe, the pressure applied by the ultrasound probe can be controlled by adjusting the load applied to the driving unit (321). The pressure that the ultrasound probe applies to the body portion can be 0-50 mmHg, preferably 5-30 mmHg.

The ultrasonic probe can be maintained in the position where the size of the organ (for example, superficial vein) to be inserted by a needle is seen in the largest size. If the organ to be inserted by a needle is not recognized, the image acquisition unit (20) is moved to other location and the detection of the organ is resumed. At first, the detection is performed at the center of the body portion. If the organ to be inserted by a needle is not detected at the center, the image acquisition unit (20) can be moved to the lateral location from the center in the 1-1 direction and the detection at the location is performed. In the embodiments that the module for z direction is provided, if the second detection fails, the image acquisition unit (20) can be moved away from the center in z direction to perform further detection. If the detection fails a predetermined number of times, it can be treated as a failure of detecting superficial vein.

A portion of the ultrasound probe can be spaced apart from the body portion since the surface of the probe is plane unlike the body portion which is not plane. The 1-3 driving unit rotates the ultrasound probe (20) on xy plane so that the probe comes into contact with the body portion and then an image of the inside of the body can be obtained.

According to the present disclosure, the pressure applied to the body by the ultrasound probe can be measured and the measured pressure can be used in machine learning, thereby making it possible to perform machine learning about relationship among the optimal pressure, optimal pressing duration, optimal pressing location, and the like. Those data can be used as additional learning information for accurately classifying the anatomical structures observed in the ultrasound image. For example, the pressure where just a vein and subcutaneous fat are pressed, the pressure where muscle is pressed, the pressure where artery is pressed, and the like can be used as learning information, thereby increasing the accuracy of machine learning.

The accurate position of the image acquisition unit (20) and the insertion unit (40) should be obtained for operation of the device of the present disclosure.

The controller of the device can calculate the position of each component based on the dimension of the components and the control value of the driving unit (for example, output value). The method for calculating the position can be conceived from the conventional techniques and thus, the description thereof is omitted since it is not essential to the present disclosure.

The position of each component can be determined by a sensor or a camera. For example, the distance between the components can be determined by two or more cameras (not illustrated). Alternatively, the position can be determined by a distance sensor or a position sensor. The sensor can be an infrared sensor or a laser sensor. The distance sensor can measure the distance between the components which are moved by the driving unit. The position sensor detects whether the components are disposed at the predetermined position.

If the position calculated by the controller is different from that obtained by the sensor or the camera, the calculated position can be replaced by the position obtained by the sensor or the camera.

After the location of the superficial vein is determined by the image analysis and machine learning, the process of recognizing the extending direction of blood vessel can be performed. The extending direction of blood vessel can be recognized by analyzing the image obtained during the movement of the image acquisition unit (20) in the longitudinal direction of the body portion, i.e., z direction, or by analyzing the image obtained after the image acquisition unit (20) rotates about y axis. Additional module and/or rotation module (not illustrated) can be necessary for determining the extending direction of blood vessel.

It is not essential to recognize the extending direction of blood vessel in the present disclosure unlike the conventional blood collection performed by a medical staff. However, the recognition of the extending direction of blood vessel can increase the possibility of success of inserting needle.

In the step (520), after the superficial vein is identified by the above-mentioned processes, at least one of the 2-1 driving unit (515) to the 2-3 driving unit (536) moves the insertion unit (40) to the position close to the superficial vein. In the step (530), the needle (45) is further moved in the 2-3 direction; is inserted to the vein; and then the blood is collected by pulling a piston (43). A module for moving the piston (43) is not illustrated for brevity of illustration. A sensor for detecting the blood inflow to the insertion unit can be provided for detecting whether blood collection succeeds. It is preferred that the location of blood vessel is monitored during blood collection. Thus, it is preferred that the needle is inserted in the 2-3 direction while the ultrasound probe (20) is in contact with the object to be inserted by a needle.

According to the present disclosure, the inserting path of the needle (45) and the extending direction of blood vessel do not need to be on the same plane. In general, a medical staff who performs blood collection inserts a needle into a body at a small angle with respect to the skin with aligning the inserting path with the extending direction of blood vessel. It causes problems that the blood vessel is pushed, and the wall of blood vessel is scraped to be damaged. However, according to the present disclosure, the needle can be inserted at a relatively large angle with respect to the skin and to the appropriate penetration depth since the image of blood vessel, the needle-inserting angle and the needle-location are monitored in real time through the analysis of the image obtained by the image acquisition unit (20). Further, the invasive range can be minimized according to the present disclosure.

It is also the advantage of the present disclosure that the inserting angle of the needle (45) does not need to be aligned with the extending path of blood vessel and does not need to be disposed on the plane of the ultrasound probe.

In the event that the image acquisition unit (20) is a photoacoustic imaging device which does not require to be in contact with something, the needle (45) can be inserted into a blood vessel and collect blood in the state that the image acquisition unit (20) is not in contact with the body portion to be inserted by a needle. In that case, the needle (45) can be inserted at an angle which is nearly perpendicular to the skin, thereby more minimizing the invasive range.

Although the present disclosure has been described with reference to accompanying drawings, the scope of the present disclosure is determined by the claims described below and should not be interpreted as being restricted by the embodiments and/or drawings described above. It should be clearly understood that improvements, changes and modifications of the present disclosure disclosed in the claims and apparent to those skilled in the art also fall within the scope of the present disclosure. Accordingly, this description is to be taken only by way of example and not to otherwise limit the scope of the embodiments herein.

What is claimed is:

1. A body-insertion device for a body, comprising:
a frame comprising a pair of posts and a horizontal bar, the pair of posts being spaced apart from each other in a transverse direction of the body in a body placing unit, and the horizontal bar extending in the transverse direction between the pair of posts;
an image acquisition unit configured to acquire to an image of the body in the body placing unit;
a first moving unit for moving the image acquisition unit, the first moving unit comprising a first guide extending in a 1-1 direction and being fixed at a first guide fixing portion of the horizontal bar;
an insertion unit comprising a needle which is configured to be inserted into the body in the body placing unit; and
a second moving unit for moving the insertion unit, the second moving unit comprising a second guide extending in a 2-1 direction and being fixed at a second guide fixing portion of the horizontal bar, wherein the second guide fixing portion of the horizontal bar is positioned apart from the first guide fixing portion in a longitudinal direction of the body in the body placing unit,
wherein the first moving unit further comprises a 1-1 module for moving the image acquisition unit in the 1-1 direction and which is connected to the horizontal bar through a first fixing portion, a 1-2 module for moving the image acquisition unit in a 1-2 direction, and a 1-3 module for moving the image acquisition unit in a 1-3 direction and which is connected to the 1-1 module and the 1-2 module,
wherein the second moving unit further comprises a 2-1 module for moving the insertion unit in the 2-1 direction and which is connected to the horizontal bar, a 2-2 module for moving the insertion unit in a 2-2 direction, and a 2-3 module for moving the insertion unit in a 2-3 direction,
wherein the 1-1 module is configured to slidably connect to the first guide, and the 1-2 module comprises a third guide extending in the 1-2 direction and to which the image acquisition unit is connected,
wherein the 1-1 module comprises a pair of spaced first pulleys, a first timing belt which extends between the first pulleys according to the 1-1 direction, a first driving unit configured to rotate the first pulleys, and a first connecting portion of the first timing belt to which the 1-3 module is connected,
wherein the 1-2 module further comprises a pair of spaced second pulleys, a second timing belt which extends between the pair of pulleys according to the 1-2 direction, a second driving unit configured to rotate the second pulleys, a first body portion to which the 1-3 module is connected,
wherein the third guide is provided in the first body portion,
wherein the 1-3 module comprises an output shaft which is connected to the first body portion, and a third driving unit configured to rotate the output shaft,
wherein the 2-1 module comprises a first movable member which moves in the 2-1 direction and is connected to the 2-2 module, the 2-2 module comprises a second movable member which moves in the 2-2 direction and is connected to the 2-3 module, and the 2-3 module comprises a third movable member connected to the insertion unit,
wherein the 2-1 module further comprises a first screw extending in the 2-1 direction, the first movable member configured to move along the first screw when the first screw rotates, a second body portion, and a fourth driving unit,
wherein the 2-2 module further comprises a second screw extending in the 2-3 direction, the second movable member configured to move along the second screw when the second screw rotates, a third body portion, a fifth driving unit, and a first fixing portion to which the first movable member is fixed, wherein the 2-3 module further comprises a third screw extending in the 2-3 direction, a third movable member, a fourth body portion, a second fixing portion to which the second movable is fixed, a sixth driving unit, and a fourth guide which extends along the 2-3 direction and is provided at the fourth body portion, and wherein the image acquisition unit comprises an ultrasound probe, a photoacoustic imaging device, or a time of flight (ToF) sensor comprising a near-infrared light emitting diode for recognizing the position coordinate of light reflected from the inside of the body.

2. The device according to claim 1, wherein the 1-1 direction is a transverse direction of a body portion to be inserted, the 1-2 direction is a height direction of the body portion, and the 1-3 direction is a rotation direction which is a longitudinal direction of the body portion.

3. The device according to claim 1, wherein the 2-1 direction is the transverse direction of the body, the 2-2 direction is a height direction of the body, and the 2-3 direction is a direction having a predetermined angle downward with respect to the 1-3 direction.

4. A computer-implemented method for controlling the device of claim 1, the method comprising:

a first step of moving the image acquisition unit to the body by driving at least one of the 1-1 module to the 1-3 module;

a second step of determining the location of the body based on the analysis of the image acquired by the image acquisition unit;

a third step of inserting a medical instrument of the insertion unit at the determined location by driving at least one of the 2-1 module to the 2-3 module, a fourth step of measuring the pressure applied to the body by the image acquisition unit, and a fifth step of performing machine learning to identify an optimal pressure, an optimal pressing duration, and an optimal pressing location by using the measured pressure and the image corresponding to the measured pressure.

5. The method according to claim 4, further comprising a sixth step of recognizing an extending path of the organ by rotating the image acquisition unit about the 1-2 direction or moving the image acquisition unit along the longitudinal direction of the body.

6. A non-transitory computer-readable media storing computer-executable instructions that, when executed by a computer, cause the one or more processors to execute the method of claim 4.

7. A computer-implemented system comprising:

the body-insertion device of claim 1;

one or more processors and one or more non-transitory computer-readable media storing computer-executable instructions that, when executed, cause the one or more processors to:

move the image acquisition unit to the body by driving at least one of the 1-1 module to the 1-3 module;

determine the location of the body based on the analysis of the image acquired by the image acquisition unit;

a third step of inserting a medical instrument of the insertion unit at the determined location by driving at least one of the 2-1 module to the 2-3 module, a fourth step of measuring the pressure applied to the body by the image acquisition unit, and a fifth step of performing machine learning to identify optimal pressure, optimal pressing duration and optimal pressing location by using the measured pressure and the image corresponding to the measured pressure.

* * * * *